US00PP09524P

United States Patent [19]

Austin

[11] Patent Number: Plant 9,524

[45] Date of Patent: Apr. 30, 1996

[54] SHRUB ROSE PLANT NAMED 'AUSMOL'

[75] Inventor: David C. H. Austin, Albrighton, England

[73] Assignee: David Austin Roses Limited, England

[21] Appl. No.: 404,160

[22] Filed: Mar. 14, 1995

[30] Foreign Application Priority Data

May 20, 1994 [FR] France ..... 13475

[51] Int. Cl.[6] ..... A01H 5/00

[52] U.S. Cl. ..... Plt./1

[58] Field of Search ..... Plt./1, 24

[56] References Cited

U.S. PATENT DOCUMENTS

P.P. 8,688 4/1994 Austin ..... Plt./1
P.P. 9,007 12/1994 Austin ..... Plt./1
P.P. 9,008 12/1994 Austin ..... Plt./1

*Primary Examiner*—Howard J. Locker
*Attorney, Agent, or Firm*—Klarquist Sparkman Campbell Leight & Whinston

[57] ABSTRACT

A shrub rose having repeat flowering with rich yellow old fashioned shaped flowers.

1 Drawing Sheet

The present invention relates to a new and distinct variety of rose plant of the shrub class which was originated by me by crossing the variety Graham Thomas with an unnamed seedling.

The primary objective of this breeding was to produce a new rose variety having yellow repeat-flowering shrub with old-fashioned-shaped flowers. The objective was substantially achieved, along with other desirable improvements, as evidenced by the following unique combination of characteristics that are outstanding in the new variety and that distinguish it from its parents, as well as from all other varieties of which I am aware:

1. Rich yellow flowers.
2. Old-fashioned shape of flower.
3. Good repeat flowering.

Asexual reproduction of this new variety by budding, as performed at Albrighton, Wolverhampton, England shows that the foregoing and all other characteristics and distinctions come true to form and are established and transmitted through succeeding propagations.

The accompnaying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Graham Thomas.

*Pollen parent.*—Unnamed seedling.

Classification:

*Botanical.*—*Rosa hybrida.*

*Commerical.*—Shrub.

FLOWER

Observations made from specimens grown in a garden environment at Albrighton, Wolverhampton, England in the United Kingdom.

Blooming habit: Recurrent.

Bud:

*Size.*—About 2.0–2.5 cm long when the petals start to unfurl.

*Form.*—The bud form is pointed ovoid and globular.

*Color.*—When sepals first divide, bud color is Red Group 51A. When half blown, the upper sides of the petals are Yellow Group 12A; and the lower sides of the petals are Yellow Group 12B.

*Sepals.*—Color: Yellow-green Group 144A/B. Surface texture: Smooth. There are three (3) lightly appendaged glandular sepals. There are two unappendaged sepals with smooth, downy, hairy edges.

*Receptacle.*—Color: Yellow-green Group 144A. Shape: Funnel. Size: Small-Medium, about 6–8 mm long×9–10 mm wide. Surface: Smooth.

*Peduncle.*—Length: Medium, averaging about 3.5–4.5 cm. Surface: Smooth, glandular. Color: Older buds and flowers, medium green; young buds, bronzy. Strength: Erect.

Bloom:

*Size.*—Medium. Average open size is about 7.0 cm.

*Borne.*—In clusters of irregular shape.

*Stems.*—Medium to normal. Average length is about 60–70 cm.

*Form.*—When first open: Bloom is cupped rosette, flat. Permanence: Retains its form to the end, flattens slightly when finished blooming, outer petal edges curl slightly.

*Petalage.*—Number of petals under normal conditions: 110–120.

*Color.*—The upper side of the petals at their top is Yellow Group 9B; at their Center and base they are Yellow Group 12B. The inner petals of the new bloom are tinged with red blush Organge-red Group 30B. The reverse side of the petals is Yellow Group 9C. The base of each petal at its tip is deep yellow. The major color on the upper side is Yellow Group 12B.

*Variegations.*—Outer edge of the middle petals of blooming flowers often have a Yellow Group 2B colouring.

*Discoloration.*—The general tonality at the end of the first day: Paler, the red blush disappears by the end of the first day. At the end of the third day, Yellow Group 8B at base of petal fading to Yellow Group 8D at outer edge.

*Fragrance.*—Slight.

Petals:

*Texture.*—Silky, thick.

*Shape.*—Slightly notched, deltoid.

*Form.*—Nearly entire tips slightly recurved.

*Arrangement.*—Informal, with no petaloids in the center.

*Persistence.*—Petals drop off cleanly before drying.

*Lastingness.*—On the plant: Long, about 3–4 days. As a cut flower: Long, about 4 days.

Reproductive parts:

*Anthers.*—Size: Medium. Quantity: Few. Color: Yellow. Arrangement: Tucked in calyx or partly so.

*Filaments.*—Color: Yellow.

*Pollen.*—Color: Gold Yellow.

*Styles.*—Color: Greenish-white.

*Stigmas.*—Color: Yellow with deep pink blush.

Form: Shrub.

Growth: Vigorous. At maturity average height is about 90 cm and width about 60 cm.

Foliage:

*Number of leaflets on normal mid-stem leaves.*— Five (5).

*Size.*—Large, about 17–19 cm long× 13 cm wide.

*Quantity.*—Normal.

*Color.*—New foliage: Yellow-green Group 146A with marked reddish blush on margins and veins. Old foliage; yellow-green Group 147A.

Leaflets:

*Shape.*—Broadly oval to pointed oval.

*Texture.*—Upper side: Leathery.

*Edge.*—Serrated.

*Serration.*—Double.

*Petiole rachis.*—Color: Green.

*Petiole underside.*—With prickles, 2–5 per internode.

*Stipules.*—Medium, serrated, about 2.5 cm long.

*Disease resistance.*—Resistant to mildew and blackspot under normal growing conditions at Albrighton, Wolverhampton, England.

Wood:

*New wood.*—Color: Reddish. Bark: Smooth.

*Old wood.*—Color: Green. Bark: Smooth.

Prickles:

*Quantity.*–On main canes from base: Few to ordinary. On laterals from main canes: Few.

*Form.*—Medium, hooked downward

*Color when young.*—Red.

*Position.*—Evenly distributed around stem, more on lower internodes.

Small prickles: None.

I claim:

1. A new and distinct variety of rose plant of the shrub class, substantially as herein shown and described, characterized particularly as to novelty by its repeat flowering with rich yellow, old fashioned shaped flowers.

* * * * *

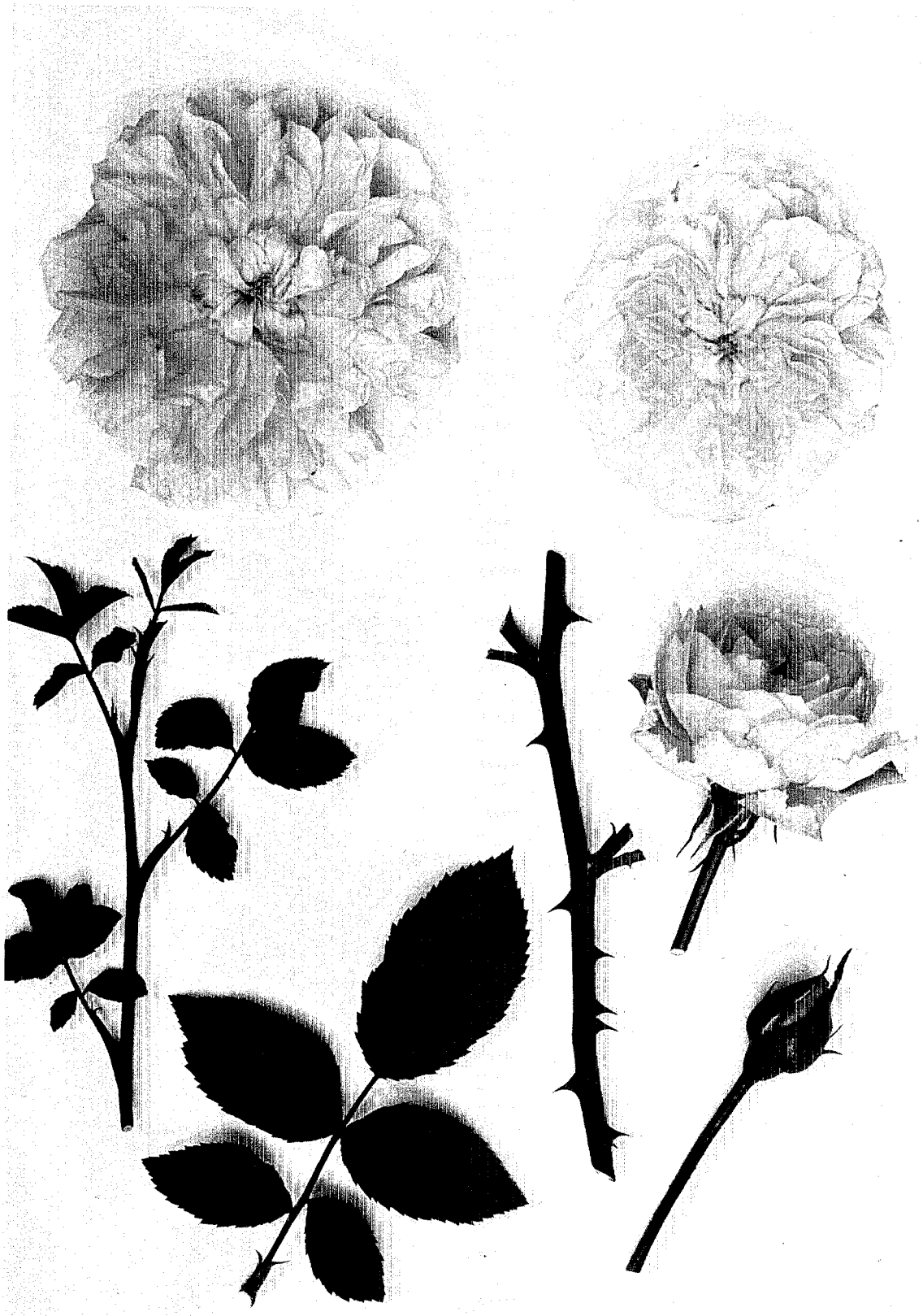
N52/83

UNITED STATES PATENT AND TRADEMARK OFFICE

CERTIFICATE OF CORRECTION

PATENT NO. : PP09524

DATED : April 30, 1996

INVENTOR(S) : David C. H. Austin

It is certified that error appears in the above-indentified patent and that said Letters Patent is hereby corrected as shown below:

Col. 1, line 21, change "accompnaying" to --accompanying--.

Col. 2, line 8, delete ", hairy".

Col. 2, line 28, before "the inner petals" insert the following sentence --The central petals are Yellow-Orange Group 15B--.

-Col. 2, line 29, change "Organge-Red" to --Orange-Red--.

Col. 2, line 38-39, delete "the red blush disappears by the end of the first day" and insert in place thereof --less red--.

Col. 3, line 23, change "yellow" to --Yellow--.

Signed and Sealed this

Twenty-second Day of April, 1997

Bruce Lehman

*Attest:*

BRUCE LEHMAN

*Commissioner of Patents and Trademarks*

*Attesting Officer*